United States Patent [19]

Iino et al.

[11] Patent Number: 4,959,104
[45] Date of Patent: Sep. 25, 1990

[54] SELF-HARDENABLE MATERIAL

[75] Inventors: Shinji Iino; Minoru Oshima, both of Yamaguchi; Shinya Kitoh, Kanagawa; Toshiaki Kobayashi, Kanagawa, all of Japan

[73] Assignees: Mitsui Toatsu Chemicals Inc.; Lion Corporation, both of Tokyo, Japan

[21] Appl. No.: 287,695

[22] Filed: Dec. 20, 1988

Related U.S. Application Data

[63] Continuation of Ser. No. 916,603, Oct. 8, 1986, abandoned.

[30] Foreign Application Priority Data

Oct. 11, 1985 [JP] Japan ................... 60-226357

[51] Int. Cl.$^5$ .............................................. C04B 12/02
[52] U.S. Cl. ...................................... 106/85; 106/35; 501/1; 501/151
[58] Field of Search .................. 501/1, 10; 106/35, 85

[56] References Cited

U.S. PATENT DOCUMENTS

| | | | |
|---|---|---|---|
| 2,099,367 | 11/1937 | Lefranc | 106/35 |
| 3,873,327 | 3/1975 | Duff | 106/35 |
| 4,224,072 | 9/1980 | Stewart | 106/35 |
| 4,542,167 | 9/1985 | Aoki | 523/109 |
| 4,565,691 | 1/1986 | Jackson | 424/52 |
| 4,612,053 | 9/1986 | Brown et al. | 106/35 |

FOREIGN PATENT DOCUMENTS

| | | | |
|---|---|---|---|
| 58-83605 | 5/1983 | Japan | 106/35 |
| 59-88351 | 5/1984 | Japan . | |
| 59-182263 | 10/1984 | Japan . | |

OTHER PUBLICATIONS

*Chemical Abstract* No. 204254h, vol. 89, No. 24, Dec. 1978, p. 420.
*Chemical Abstract* No. 115875k, vol. 101, No. 14, Oct. 1, 1984, p. 294.
"Effect of Additives on Hydration and Hardening of Tricalcium Phosphate", Hideki Monma, Masaru Goto and Tamotsu Kohmura, *Gypsum & Lime* No. 188, pp. 11-16, (1984).

*Primary Examiner*—Mark L. Bell
*Attorney, Agent, or Firm*—Jeffers, Hoffman & Niewyk

[57] ABSTRACT

A self-hardenable material comprising a calcium phosphate having an atomic ratio of Ca/P of 1.4 to 1.6, a difficultly water-soluble inorganic fluoride, an organic or inorganic acid and water is provided. For example, when the hardenable material is frilled in the form of slurry or paste in a necessary part in vivo or in the dental cavity, it hardens within a short time to form a stable apatite type product.

8 Claims, No Drawings

SELF-HARDENABLE MATERIAL

This is a continuation of application Ser. No. 916,603, filed Oct. 8, 1986, now abandoned.

BACKGROUND OF THE INVENTION

1. Field of the Invention

This invention relates to a self-hardenable material. More particularly it relates to a self-hardenable material forming a fluoro-apatite type product and useful for example as materials for substitutes or fillers of living body.

2. Description of Related Art

Calcium-phosphorus apatite as a kind of calcium phosphates (hereinafter referred to merely as apatite) is expressed by a theoretical formula $Ca_{10}(PO_4)_6X_2$ (wherein X represents an anion such as $OH^{-1}$, $Cl^{-1}$, $F^-$, etc.) Here, the g•atom ratio of Ca/P is theoretically $10/6=1.67$, but it has been regarded that practically the apatite structure can be formed in a Ca/P ratio in the range of 1.3 to 2.0.

Thus, various general formulas have been proposed, and for example, $Ca_{10-y}(HPO_4)_y(PO_4)_{6-y}X_{2-y}$ is illustrated, wherein X is as defined above and y is a number of 0 to 2.

This apatite is a main component of mineral ones of teeth or bones and so superior in the affinity in vivo that it easily assimilates with the tissues of living body; hence its utilization as a tooth implant or a filler for bone defect part has been energetically studied. However, in spite of the excellent affinity of the apatite with living body, it is the present due to the following reason status that its utilization as materials for living body such as dental materials, medical materials, etc. has been very small.

Heretofore, as to the utilization of the apatite as materials for living body, there has been mainly employed a method of molding hydroxyapatite powder according to press molding, cast molding or the like molding, followed by calcining the resulting material into ceramics to obtain a desired molded product. However, according to such a molding method, it is difficult to mold such a material into a product having a complicated shape so that it has been practically impossible to correspond to cases where molded products having various shapes and dimensions depending upon individual remedies are required.

On the other hand, among hardenable materials for living body so far used, there are dental cement, dental composite resins, bone cement, etc.

These hardenable materials have been used in such a manner that they are in the form of paste or slurry at the time of their use, and after they have been filled in necessary parts in dental cavity or in vivo, they are hardened. Thus, these hardenable materials can be molded into an optimum shape depending upon individual remedies.

However, these conventional dental cement, composite resins, bone cement, etc. comprise components which are substances different from the hard tissue of living body, that is, inorganic and organic substances such as zinc oxide, silica powder, polyacrylate, eugenol, etc.; hence the conventional materials have defects of being difficultly operated in the aspect of stringiness or viscous properties. Further, the materials are fixed merely by a physical or chemical adhesion to living body; hence no assimilation with the tissue of living body occurs.

Thus, a method has been proposed which comprises filling a kneaded material in the form of slurry, composed mainly of a calcium phosphate convertible into apatite, in necessary parts in vivo or in the oral cavity, followed by hardening the material within a short time to form an apatite structure (Japanese patent application laid-open Nos. Sho 59-88351 and Sho 59-182263). According to the art disclosed in the laid-open gazettes, it is possible to form an apatite type hardened product at a temperature in the vicinity of that of living body within a relatively short time, by adding an organic or inorganic acid and an easily water-soluble halide to α-calcium triphosphate.

However, in order to practically use the apatite type hardened product obtained according to the above art, the following problems to be solved are left behind:

(1) The resulting hardened product has a hardness as low as about 6 kg/mm$^2$ at the highest in terms of Knoop hardness.

(2) The hardened product has a very low stability in water and readily collapses.

(3) Its shrinkage at the time of hardening is so large that it is deficient in dimensional accuracy to make it difficult to adapt it to defect parts.

SUMMARY OF THE INVENTION

An object of the present invention is to provide a hardenable material useful as a substitute or filler for living body, which is filled in a necessary part in vivo or in the dental cavity and hardened at the temperature of living body within a relatively short time to make it possible to assimilate with the tissue of living body.

Another object of the present invention is to provide a hardenable material which can afford an apatite hardened product which has a high hardness, does not collapse in water, has a good stability and has a dimensional accuracy due to a small shrinkage of the curing material at the time of its curing.

The present invention resides in a hardenable material comprising a self-hydraulic calcium phosphate having a g•atom ratio of Ca/P of 1.3 to 2.0, a difficultly water-soluble inorganic fluoride, acids and water.

According to the present invention, an apatite precursor substance in the form of slurry or paste at the time of its use is filled in a defect part of teeth or bones having a complicated shape and the filled substance is hardened within a relatively short time to form an apatite hardened product having a high hardness which then comes to have a high assimilability with the tissue of living body with lapse of time.

DETAILED DESCRIPTION OF PREFERRED EMBODIMENTS

As the self-hydraulic calcium phosphates used in the present invention, those obtained by calcination at 700°~1,400° C., preferably 900°~1,300° C. for 1 to 10 hours, preferably 2 to 4 hours are preferred. Among these calcium phosphates, calcium triphosphate is particularly preferred. In the case where a product obtained by calcination at temperatures outside the above range is used, there is a tendency that the conversion rate of the calcium phosphates into the apatite type product lowers.

Further, the g•atom ratio of Ca/P of calcium phosphates is within the range of 1.3 to 2.0, preferably 1.4 to 1.6.

If calcium phosphates having a g•atom ratio of Ca/P outside the range of 1.3 to 2.0 are used, since the difference between such ratio and the Ca/P ratio in the theoretical composition of apatite is too large, conversion of such calcium phosphates into apatite structure by hardening is difficult and accordingly, hardened products of good properties cannot be obtained even if the calcium phosphate is mixed with an acidic hardening accelerator and kneaded together.

Next, as an accelerator for converting the calcium phosphates under the above conditions into apatite in water, difficultly water-soluble inorganic fluorides are used. If easily water-soluble inorganic fluorides such as alkali metal salts are used, only a cured product having a low hardness is obtained.

As such difficultly water-soluble inorganic fluorides, alkaline earth metal salts of hydrofluoric acid such as calcium fluoride, magnesium fluoride, beryllium fluoride, strontium fluoride, barium fluoride, etc. are preferred. Such fluorides may be those wherein the fluorine contained therein is incorporated into the calcium phosphates to form a fluoroapatite.

Further, in the present invention, other inorganic fluorides may be used, if desired, in an amount of two times moles or less in addition to the above fluorides thereby improving a dimensional stability of the cured product. Examples of such fluorides are alkali metal salts of hydrofluoric acid such as sodium fluoride, lithium fluoride, potassium fluoride, cesium fluoride, rubidium fluoride, ammonium fluoride, ammonium hydrogenfluoride, etc. Among these, ammonium fluoride and ammonium hydrogenfluoride are particularly preferred.

The apatite type hardened product obtained from the hardenable material of the present invention has been confirmed to form a fluoro-apatite by x-ray diffraction. This fluorinated apatite has been known to have a particularly stable form among those of apatites; thus it will be readily understood that this hardened product exhibits a superior stability in vivo or in the dental cavity.

In the present invention, acids such as an organic or inorganic acid are used as an accelerator in addition to the above fluoride.

Examples of such an organic acid are lower monobasic fatty acids such as formic acid, acetic acid, propionic acid, etc.; hydroxycarboxylic acids such as malic acid, glycolic acid, lactc acid, citric acid, saccharic acid, ascorbic acid, etc.; acidic amino acids such as glutamic acid, asparagic acid, etc.; dibasic acids such as oxalic acid, malonic acid, succinic acid, glutaric acid, adipic acid, maleic acid, fumaric acid, muconic acid, etc.; keto acids such as pyrubic acid, acetoacetic acid, levulinic acid, etc.; aromatic carboxylic acids such as salicylic acid, benzoic acid, cinnamic acid, phthalic acid, etc.; alkali metal salts, alkaline earth metal salts or ammonium salts of the foregoing organic acids; derivatives of the foregoing organic acids which easily form a carboxylic group by hydrolysis such as acid anhydrides, acid chlorides, etc.; etc.

Examples of the above-mentioned inorganic acid are phosphoric acid, hydrochloric acid, nitric acid, and sulfuric acid and also, salts thereof such as an alkali metal, alkaline earth metal or ammonium salt may be used.

These acids give the effectiveness of shortening the hardening time and increasing the hardness of the hardened product. When these acids are used in the form of an aqueous solution as the hardening accelerator, the pH thereof is preferred to be in the range of 2.5 to 6.0 and more preferred to be in the range of about 3.0 to 5.0, in view of the curing rate, physical properties of the resulting product, etc.

In the preparation of the hardenable material of the present invention, the respective components may be individually prepared, followed by kneading and hardening them at the time of its use to form the objective product, but taking into account the convenience of practical handling, it is preferred for example to individually prepare the following powder component and liquid component, followed by kneading and hardening them at the time of their use to form the objective hardened product:

The representative cases are illustrated as follows:

(i) a case where the powder component consists of calcium phosphate, an inorganic fluoride and an acid and the liquid component is water;

(ii) a case where the powder component consists of calcium, phosphate and an inorganic fluoride and the liquid component is an aqueous solution of acid; and (iii) a case where the powder component is calcium phosphate and a difficultly water-soluble inorganic fluoride and the liquid component is an aqueous solution of acid and a water-soluble inorganic fluoride. However, cases are, of course, not limited to these cases.

As to the ratio by weight of such a powder component to such a liquid component, it is preferred to mix these components in a ratio of 10.0:2.0 to 10.0:5.0 and use the mixture.

The quantity of the acid(s) relative to calcium phosphate is preferred to be in the range of about $2 \times 10^{-5}$ mol/g to $2 \times 10^{-3}$ mol/g.

In addition, in the case where the powder component consists of calcium phosphate and an inorganic fluoride and the liquid component is an aqueous solution of acid(s), it is preferred to add the aqueous solution of acid(s) having a concentration of 0.1 mol/l to 2.5 mol/l to the powder component and knead them.

As to the quantity of the difficultly water-soluble inorganic fluoride, the g•atom ratio of Ca/F is to be at least 4.2 in view of the necessity that fluorine should be incorporated into apatite, but in order that the hardening time is several hours or shorter, the practical upper limit of the g•atom ratio of Ca/F is about 60.

Further, the hardening material of the present invention include water to advance the hardening reaction. The amount of water is theoretically at least $\frac{1}{3}$ mol relative to one mol of $PO_4$ in the aspect of the hardening reaction. However, taking into account the kneadability, operability, etc., it is possible to use a suitable quantity of water more than the above quantity and normally, the mole ratio of $H_2O/PO_4$ of $\frac{1}{3}$ to 50 is preferred.

As mentioned above, the components of a calcium phosphate having a ratio of Ca/P of 1.3 to 2.0, a difficultly water-soluble inorganic fluoride, an acid and water, constituting the hardenable material of the present invention are mixed in the indicated ratios and the mixture are kneaded and allowed to stand to give a fluoro-apatite type hardened product by self-hydraulicity (or self-hydration hardening).

In order to use such an apatite product for example as a substituting or filling material for living body, if the time required for the self-hardening is too long or too short, the clinical operation becomes difficult. Thus it is desired that the time required for the hardening can be controlled easily and to a large extent depending upon the object of its use. According to the hardenable material of the present invention, it is possible to vary the hardening time at a relatively low temperature in the vicinity of the temperature of living body in a time range of about 5 minutes to several hours by adjusting a pH of the acid solution and amount of the acid.

In the case of so far used cement hardened products consisting of an inorganic powder and a liquid component containing a water-soluble high molecular weight polymer, the viscous properties originating from the water-soluble high molecular weight polymer have, in most cases, made the kneading operation and the clinical operation difficult. Whereas, in the case of the hardened product made from the hardenable material of the present invention, since no high molecular weight polymer is used, the problems of viscous properties or stringiness as described above are not raised so that its operations are easy and such facts are characteristics of the hardened product.

Further, since the hardened product made by the hardenable material of the present invention hardly shrinks during the hardening process, no clearance occurs at the interface between living body and the filler used for filling the defect of living body; hence this is notably advantageous to its compatibility with living body.

For the material for living body, two fundamental functions are required. One of the functions is its mechanical strengths in the aspect of material and another is its bio-compatibility. The mechanical strengths include hardness, compression strength, bending strength, etc., and in order to obtain a sufficient mechanical strength, it is indispensable that the resulting product has been sufficiently hardened. Although it is difficult to reproduce the environment wherein the material for living body is used, in vitro, it was observed whether or not the hardened product according to the present invention was preserved in water to cause collapse, in order to examine whether or not the product according to the present invention could retain the functional strengths of the material when it was applied to living body. As a result, the hardened product maintained its shape without causing collapse. Further, the hardness of the product expressing its physical properties was measured. As a result, any of the measured products had values around 15 kg/mm$^2$ in terms of Knoop hardness. Moreover, it is to be noted that when the product was preserved in an artificial saliva in place of water, the surface hardness increased with lapse of time and a product having a hardness amounting to 40 kg/mm$^2$ in terms of Knoop hardness was observed. Thus, it was evidenced that the hardened product obtained from the hardenable material of the present invention continued to be improved in its physical properties in the aspect of mechanical strengths; hence the material can be said to be an excellent material for living body.

Further, in order to examine the bio-compatibility of the hardened product based on the present invention to living body, a defect was artificially prepared in the lower jaw of a male SD rat, followed by press-filling the kneaded product and observing it with lapse of time. As a result, no fibrous connective-tissue intervened, inflammatory cells disappeared with lapse of time and formation of bone tissue was observed; thus it was clarified that the hardenable material was very excellent as a material for living body.

The present invention will be described in more detail by way of Examples.

EXAMPLE 1

An aqueous solution of 1M citric acid adjusted to a pH of 3.0 with aqueous ammonia (0.425 ml) was added to powder consisting of $Ca_3(PO_4)_2$ burned at 1,300° C. for one hour (0.975 g) and $CaF_2$ (0.025 g) and the mixture was sufficiently kneaded. The thus kneaded material was poured in a mold obtained by combining an acrylic resin ring of 12 mm in inner diameter and 5 mm high with a glass plate placed on the bottom part of the ring. The resulting kneaded material was subjected to measurement of its caking time according to JIS T6604. Further, the time required by the time when no mark of Vicat indenter paint was left behind was made the hardening time. As a result, the caking time was 7 minutes and the hardening time was 8 minutes. Further, the hardness at 24 hours after hardening was 15 kg/mm$^2$ in terms of Knoop hardness.

Further, this cured product was preserved in the following artificial saliva kept at 37° C. to observe the change in Knoop hardness. As a result, it was 16 kg/mm$^2$ after one day and 40.0 kg/mm after 30 days. The results are collectively shown in Table 1.

| Artificial saliva Solution A: | |
| --- | --- |
| ammonium chloride (NH$_4$Cl) | 0.466 g |
| potassium chloride (KCl) | 2.324 g |
| potassium monophosphate (KH$_2$PO$_4$) | 0.708 g |
| Na$_3$(C$_6$H$_2$O$_7$).2H$_2$O | 0.0206 g |
| sodium biphosphate (Na$_2$HPO$_4$) | 0.750 g |
| and | |
| urea (NH$_2$)$_2$CO | 0.346 g | were dissolved in H$_2$O to prepare 1 l solution.

| Solution B: | |
| --- | --- |
| calcium chloride dihydrate salt (CaCl$_2$.2H$_2$O) | 0.420 g |
| and | |
| magnesium chloride (MgCl$_2$) | 0.04 g | were dissolved in H$_2$O to prepare 1 l solution. At the time of their use, solution A and solution B were mixed in a ratio by volume of 1:1.

EXAMPLE 2~10

Using calcium phosphate, fluorides, acids and kneading solutions each in definite quantities and employing definite ratios of powder/liquid, as shown in Table 1, operation was carried out in the same manner as in Example 1 to prepare kneaded products, which were then subjected to measurements of caking time, hardening time, hardness and change in hardness in the artificial saliva. The results are shown in Table 1.

COMPARATIVE EXAMPLES 1 AND 2

Example 1 was repeated except that NH$_4$F•HF or NH$_4$F was used as the fluoride and conditions indicated in Table 1 were employed, to prepare kneaded products, which were then subjected to measurements of caking time, hardening time and Knoop hardness. The results are shown in Table 1.

As apparent from the results of Table 1, any of the products obtained in Examples 1~10 have a high hardness and even after they are preserved in the artificial saliva for 30 days, they cause neither collapse nor cracking and exhibit a high hardness. Whereas, in the cases of Comparative examples 1 and 2, the kneaded products have a Knoop hardness as low as 6 or less and easily cause cracking or collapse after they preserved in the artificial saliva for one day or longer; hence it is seen that they have a low stability.

Further, in any of Examples 1~10, neither stringiness nor viscous properties were observed in the kneading operation for obtaining the hardened products. Further, when the products were drawn out of the ring after the measurements of the caking time and the hardening time, they were difficult to be drawn out of the ring; hence it is seen that their shrinkage at the time of hardening is very small in any of the Examples. Furthermore, the products drawn out of the ring were preserved in water to measure their change in hardness. The results were the same as those in the case of the artificial saliva.

anhydrides or acid chlorides; and inorganic acids and their alkali metal, alkaline earth metal or ammonium salts, and said calcium phosphate being capable of converting to fluoroapatite on hardening.

2. A self-hardenable material of claim 1 wherein said Ca/P ratio is between 1.4 and 1.6.

3. A self-hardenable material of claim 1 wherein said difficultly water-soluble inorganic fluoride is an alkaline earth metal salt.

4. A self-hardenable material as described in claim 1 wherein said difficultly water-soluble inorganic fluoride is selected from the group consisting of calcium fluoride, magnesium fluoride, beryllium fluoride, strontium fluoride, and barium fluoride.

5. A self-hardenable material as described in claim 4 including other inorganic fluorides in an amount of twice the moles or less than said difficultly water-solu-

TABLE 1

| Example No. | | Calcium phosphate | | Fluoride | | Concentration of kneading solution (M) | | |
|---|---|---|---|---|---|---|---|---|
| | | Ca/P | Quantity added (g) | Kind | Quantity added (g) | Substances | Concentration (M) | pH |
| Example | 1 | 1.5 | 0.975 | $CaF_2$ | 0.025 | Citric acid | 1.0 | 3.0 |
| | 2 | " | " | $CaF_2$ | " | Glycolic acid | 1.5 | 3.0 |
| | 3 | " | 0.961 | $SrF_2$ | 0.039 | Citric acid | 1.0 | 4.0 |
| | 4 | " | 0.947 | $BaF_2$ | 0.053 | Citric acid | 1.0 | 4.0 |
| | 5 | " | 0.934 | $CaF_2$/$NH_4FHF$ | 0.032/0.034 | Citric acid | 1.0 | 5.0 |
| | 6 | " | " | $CaF_2$/$NH_4FHF$ | 0.032/0.034 | Citric acid | 2.0 | 5.0 |
| | 7 | " | 0.975 | $CaF_2$ | 0.025 | Phosphoric acid | 0.5 | 4.0 |
| | 8 | " | " | $CaF_2$ | " | Hydrochloric acid | 0.4 | 5.0 |
| | 9 | 1.6 | 1.000 | $CaF_2$ | " | Formic acid | 1.0 | 4.0 |
| | 10 | 1.4 | 0.950 | $CaF_2$ | " | Lactic acid | 1.0 | 4.0 |
| Compar. example | 1 | " | 0.982 | $NH_4FHF$ | 0.018 | Glycolic acid | 1.0 | 3.6 |
| | 2 | " | 0.977 | $NH_4F$ | 0.023 | Glycolic acid | 1.0 | 3.6 |

| Example No. | | Powder/liquid ratio ml/g | Ca/F in kneaded product | Caking time (min.) | Hardening time (min.) | Knoop hardness $kg/mm^2$ | | |
|---|---|---|---|---|---|---|---|---|
| | | | | | | 0 day | 1 day | 30 days |
| Example | 1 | 0.425 | 15.5 | 7 | 8 | 15 | 16 | 40 |
| | 2 | 0.425 | 15.5 | 38 | 49 | 15 | 14 | 35 |
| | 3 | 0.425 | 15.0 | 15 | 25 | 14 | 17 | 39 |
| | 4 | 0.425 | 15.0 | 25 | 75 | 12 | 15 | 36 |
| | 5 | 0.285 | 4.7 | 15 | 22 | 15 | 20 | 30 |
| | 6 | 0.285 | 4.7 | 5 | 13 | 15 | 22 | 31 |
| | 7 | 0.485 | 15.5 | 11 | 43 | 14 | 16 | 32 |
| | 8 | 0.462 | 15.5 | 14 | 48 | 13 | 15 | 30 |
| | 9 | 0.433 | 16.2 | 9 | 14 | 15 | 17 | 29 |
| | 10 | 0.374 | 14.2 | 23 | 64 | 14 | 21 | 33 |
| Compar. example | 1 | 0.425 | 15.0 | 15 | 25 | 6> | — | — |
| | 2 | 0.425 | 15.0 | 35 | 80 | 6> | — | — |

Note: The symbol "—" indicates that the hardened product causes cracking or collapse.

What is claimed is:

1. A self-hardenable material consisting essentially of calcium phosphate having a g atom ratio of Ca/P of 1.3 to 2.0, a difficultly water-soluble inorganic fluoride, an acid and water, the ratio of said calcium phosphate to said difficultly water-soluble fluoride being within the range of g atom ratio of Ca/F of 4.2 to 60, said acid being included in a ratio of $2 \times 10^{-5}$ mol/g to $1.2 \times 10^{-3}$ mol/g relative to calcium phosphate, said water being within a mole ratio of $H_2O/PO_4$ of ⅓ to 50, said acid being selected from the group consisting of organic acids of formic acid, acetic acid, propionic acid, glycolic acid, lactic acid, citric acid, saccharic acid, ascorbic acid, glutamic acid, asparagic acid, oxalic acid, malonic acid, succinic acid, glutaric acid, adipic acid, pyrubic acid, acetoacetic acid, levulinic acid, salicylic acid, benzoic acid, phthalic acid and their alkali metal, alkaline earth metal or ammonium salts, and their acid ble inorganic fluoride wherein said other inorganic fluorides are selected from the group consisting of sodium fluoride, lithium fluoride, potassium fluoride, cesium fluoride, rubidium fluoride, ammonium fluoride, and ammonium hydrogenfluoride.

6. A fluoro-apatite hardened product obtained by hardening a composition consisting essentially of calcium phosphate having a g atom ratio of Ca/P of 1.3 to 2.0, a difficultly water-soluble inorganic fluoride, an acid and water, the ratio of said calcium phosphate to said difficultly water-soluble fluoride being within the range of g atom ratio of Ca/F of 4.2 to 60, said acid being included in a ratio of $2 \times 10^{-5}$ mol/g to $1.2 \times 10^{-3}$ mol/g relative to calcium phosphate, said water being within a mole ratio of $H_2O/PO_4$ of ⅓ to 50, said acid being selected from the group consisting of organic acids of formic acid, acetic acid, propionic acid, glycolic acid, lactic acid, citric acid, saccharic acid, ascorbic acid, glutamic acid, asparagic acid, oxalic acid, malonic acid, succinic acid, glutaric acid, adipic acid, pyrubic acid, acetoacetic acid, levulinic acid, salicylic acid, benzoic acid, phthalic acid and their alkali metal, alkaline earth metal or ammonium salts, and their acid anhydrides or acid chlorides; and inorganic acids and their alkali metal, alkaline earth metal or ammonium salts.

7. A fluoro-apatite hardened product as described in claim 6 wherein said difficultly water-soluble inorganic fluoride is selected from the group consisting of calcium fluoride, magnesium fluoride, beryllium fluoride, strontium fluoride, and barium fluoride.

8. A fluoro-apatite hardened product as described in claim 7 including other inorganic fluorides in an amount of twice the moles or less than said difficultly water-soluble inorganic fluoride wherein said other inorganic fluorides are selected from the group consisting of sodium fluoride, lithium fluoride, potassium fluoride, cesium fluoride, rubidium fluoride, ammonium fluoride, and ammonium hydrogenfluoride.

* * * * *